US009584066B2

(12) United States Patent
Mabille

(10) Patent No.: US 9,584,066 B2
(45) Date of Patent: Feb. 28, 2017

(54) METHOD AND SYSTEM FOR CONTROLLING THE QUALITY OF A PHOTOVOLTAIC DEVICE

(71) Applicant: COMMISSARIAT A L'ENERGIE ATOMIQUE ET AUX ENERGIES ALTERNATIVES, Paris (FR)

(72) Inventor: Loïc Mabille, La Motte-Servolex (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 0 days.

(21) Appl. No.: 14/782,511

(22) PCT Filed: Apr. 4, 2014

(86) PCT No.: PCT/EP2014/056800
§ 371 (c)(1),
(2) Date: Oct. 5, 2015

(87) PCT Pub. No.: WO2014/161983
PCT Pub. Date: Oct. 9, 2014

(65) Prior Publication Data
US 2016/0056761 A1    Feb. 25, 2016

(30) Foreign Application Priority Data

Apr. 5, 2013  (FR) ..................... 13 53055

(51) Int. Cl.
*G01N 21/00*    (2006.01)
*H02S 50/15*    (2014.01)
(Continued)

(52) U.S. Cl.
CPC ............. *H02S 50/15* (2014.12); *G01N 21/66* (2013.01); *G01N 21/9505* (2013.01); *H02S 50/10* (2014.12)

(58) Field of Classification Search
CPC .......... G01N 21/6489; G01N 21/9501; G01N 19/00; G01N 2201/06113; G01N 2201/062;
(Continued)

(56) References Cited

U.S. PATENT DOCUMENTS

2009/0206287 A1*  8/2009  Trupke ............... G01N 21/6489
                                                          250/582
2011/0153228 A1*  6/2011  Ahmad .............. G01N 21/9505
                                                          702/40
(Continued)

FOREIGN PATENT DOCUMENTS

| EP | 2 343 534 A1 | 7/2011 |
| EP | 2 378 278 A1 | 10/2011 |
| JP | 2008-26113 A | 2/2008 |

OTHER PUBLICATIONS

Zimmermann, "Perfomance Mapping of Multijunction Solar Cells Based on Electroluminescence", IEEE Electron Device Letters, vol. 30, No. 8, Aug. 1, 2009, pp. 825-827; (3 pages).

(Continued)

*Primary Examiner* — Michael P Stafira
(74) *Attorney, Agent, or Firm* — Westerman, Hattori, Daniels & Adrian, LLP

(57) ABSTRACT

The photovoltaic device comprises a photovoltaic cell (1) assembled with a substrate (2) by way of an assembly interface. The method comprises a step of injecting an electrical current through the photovoltaic cell and a step of acquiring a signal measuring the luminous radiation emitted by the photovoltaic cell (1), by electroluminescence, in response to the injected current. The injection current has a density higher than a preset assembly defect detection current threshold. A step of detecting at least one defect in the assembly interface on the basis of said acquired measuring signal is provided.

21 Claims, 4 Drawing Sheets

(51) Int. Cl.
*G01N 21/66* (2006.01)
*G01N 21/95* (2006.01)
*H02S 50/10* (2014.01)

(58) Field of Classification Search
CPC ....... G01N 2201/08; G01N 2203/0082; G01N 2203/0286; G01N 3/02; G01N 3/42; G01N 21/66; G01N 21/95607; G01N 2021/8887
See application file for complete search history.

(56) References Cited

U.S. PATENT DOCUMENTS

| | | | |
|---|---|---|---|
| 2011/0255772 A1 | 10/2011 | Zimmermann | |
| 2013/0043405 A1* | 2/2013 | Maxwell | G01N 21/6489 250/459.1 |

OTHER PUBLICATIONS

Zimmermann, "Utilizing lateral current spreading in multijunction solar cells: An alternative approach to detecting mechanical defects", Journal of Applied Physics, 100, Jul. 26, 2006, pp. 023714-1-023714-8; (8 pages).

Bosco et al., "CPV Cell Infant Mortality Study", 7th International Conference on Concentrating Photovoltaic Systems, May 2011, pp. 1-4, retrieved from the Internet: URL:http://www.nrel.gov/docs/fyllosti/51337; (6 pages).

Duggan et al., "Evaluation of Competing Triple Junction Concentrator Cells by Electroluminescence", Photovoltaic Specialists Conference, IEEE, Jun. 7, 2009, pp. 655-659; (5 pages).

International Search Report and Written Opinion dated Jul. 31, 2014 issued in counterpart application No. PCT/EP2014/056800 (w/ partial English translation and partial machine English translation) (22 pages).

* cited by examiner

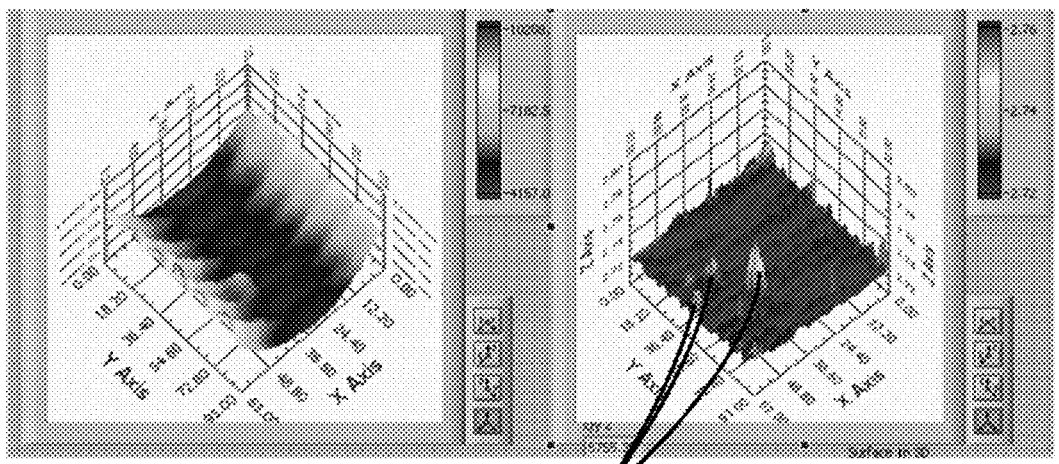
Figure 7A    11    Figure 7B

METHOD AND SYSTEM FOR CONTROLLING THE QUALITY OF A PHOTOVOLTAIC DEVICE

The invention relates to a method and system for controlling the quality of a photovoltaic device comprising a photovoltaic cell assembled with a substrate by way of an assembly interface.

A photovoltaic cell is an electronic component that, when it is subjected to light rays such as those from the Sun, generates a DC electrical current that depends on the intensity of the incident light, and a DC voltage that is dependent on the spectrum of this incident light. Photovoltaic cells are most often fabricated from one or more semiconductors—mainly based on silicon and more rarely on copper selenide or cadmium telluride. They may also be fabricated from materials from columns III and V of Mendeleev's periodic table of the elements, such as indium, gallium, phosphorus and arsenic inter alia. They generally take the form of thin plates with side lengths ranging from a few millimeters to several centimeters.

A plurality of cells may be combined in a photovoltaic solar panel, module or receiver and assembled on a substrate. For certain applications such as the field of concentrator photovoltaics (CPV), the photovoltaic cells and substrate are held together by a metal solder or an epoxy resin, inter alia.

A photovoltaic cell converts only some of the incident light, between 10 and 40% of the latter, depending on the technology used. The remaining light energy, not converted into electricity, is converted into heat and causes heating of the cell. In order to prevent overheating of the latter, the substrate is generally assembled with an energy sink. Thus, the cell is mounted at the top of a thermal dissipation chain comprising the substrate, the solder and the sink, said chain being intended to dissipate the heat produced by the light energy that is not converted into electricity.

The assembly interface between the photovoltaic cell and the substrate is a particularly critical zone of this thermal chain. Specifically, during production of this interface, by melting of the solder to use the aforementioned example, or by solidification of the resin, defects such as air holes, commonly referred to as voids, may form. These defects lead to a break in mechanical and thermal cohesion in the location where the air is trapped. This results in a decrease in the effectiveness of the thermal chain and, eventually, failure of the cell, or even destruction of the latter.

It is therefore important, at the end of the manufacturing process of the photovoltaic panel, module or receiver, to control the quality of the cell/substrate assembly interface in order to detect any void-type defects.

There are mainly two techniques for detecting voids in the assembly interface between cell and substrate:
x-ray tomography; and
infrared imaging.

The first technique yields excellent results but requires complex and expensive apparatus. The second technique requires a long thermal stabilization time and therefore is not very compatible with the constraints of industrial manufacture.

The present invention aims to improve the situation.

For this purpose, it relates to a method for controlling the quality of a photovoltaic device comprising a photovoltaic cell assembled with a substrate by way of an assembly interface, comprising the following steps:
injecting an electrical current through the photovoltaic cell; and
acquiring a signal measuring the luminous radiation emitted by the photovoltaic cell, by electroluminescence, in response to the injected current;
characterized in that the injection current is a first current having a density higher than a preset assembly defect detection current threshold, and a step of detecting at least one defect in the assembly interface on the basis of said acquired measuring signal is provided.

The main function of a photovoltaic cell is to convert photons into electrons, in other words to convert incident light into electricity. Conversely, when the cell is biased, it emits light, at one or more wavelengths set by the number of p-n junctions that the cell contains and by the materials that make up these junctions, in response to the current passing therethrough. It is a question of an electroluminescence effect that results from radiative recombination of the injected electrons and electronic holes in the material, producing photons. However, only some of the injected electrons are converted into photons. The remaining electrons, not converted into photons, recombine non-radiatively, thus causing sometimes very substantial heating of the cell.

It is known, especially from document EP2343534, to use the electroluminescence property of a photovoltaic cell to detect defects in the structure of the cell itself.

The present invention also uses the electroluminescence property of photovoltaic cells. However, in the invention, this electroluminescence property of the cell is used, in a surprising way, to detect defects present not in the cell itself but in the assembly interface between the cell and the substrate. The invention is based on an effect of modification of the electroluminescent behaviour of the cell associated with a defect in the assembly interface, newly observed by the inventors. Specifically, in the cell, when the injected current is sufficiently high, in the location positioned plumb with the defect in the assembly interface, it is possible to observe an increase in the intensity of the light radiation emitted by the cell, by electroluminescence. A defect, such as a void, also referred to as an air hole, in the assembly interface between the cell and the substrate therefore has an impact on the electroluminescent behaviour of the cell in the location positioned plumb with this defect. The invention astutely uses this effect to detect and locate defects, in particular voids, in the assembly interface, by injection of a suitable current.

Advantageously, the assembly defect detection threshold is equal to 1 A·cm$^{-2}$.

With a current of density higher than 1 A/cm$^{-2}$ it is possible to easily discern the position of a defect in the assembly interface for certain types of photovoltaic devices. The higher the injected current, the more visible defects are in the acquired image. The maximum value of the injection current may be about a few tens of amps, or even more. In any case, the injection current must be lower than a maximum value that would lead to deterioration either of the assembly interface (for example the interface will melt if the cell is excessively heated), or of the cell (for example by thermal runaway). This maximum upper value of the injection current depends on the physical characteristics of the cell and of the assembly interface.

From the acquired measuring signal it is possible to form an image representative of an emitting area of the photovoltaic cell, each image pixel being characterized by a measured physical quantity related to the light radiation emitted by the cell in response to the injected current.

The acquisition may be carried out very rapidly by taking a discrete image.

Advantageously, the first current is injected in the form of a pulse of a preset duration. Again advantageously, the duration of the current pulse is comprised between 1 ms and 10 s.

The injecting step may thus consist in applying a single current pulse to the cell.

The acquisition of the radiation signal is advantageously synchronized with this injecting step. The radiation signal is preferably acquired during the injection of an, even very brief, current pulse leading instantaneously or almost instantaneously:

- on the one hand, to emission of light by the cell, by radiative recombination of some of the injected electrons; and
- on the other hand, to heating of the cell, by non-radiative recombination of the remaining electrons.

All that is required to detect any defects in the assembly interface on the basis of the acquired luminous radiation signal is to inject a current pulse. Thus, surprisingly, to detect any assembly interface defects, it is not necessary to inject the current for a time long enough to allow the cell to spread the heat flux caused by the injection of electrons throughout the thermal chain, nor to wait for thermal stabilization of the latter.

The method of the invention may comprise all or some of the following additional features:

- the method comprises an operation of processing the acquired image, in which at least one image zone corresponding to a peak of said measured physical quantity is detected, the image pixels inside said zone being characterized by measured physical quantities higher than a preset threshold;
- the processing operation comprises a thresholding step that produces an image the pixels of which are associated with one or other of two preset values, depending on whether the measured physical quantity characterizing the pixel in question is lower or higher than a preset threshold;
- the processing operation comprises a step of recognizing shapes in the image in order to detect at least one ellipse-shaped zone;
- the method furthermore comprises a step of injecting a second electrical current through the photovoltaic cell, said second current having a density lower than said preset current threshold, followed by a step of acquiring a measuring signal related to the luminous radiation emitted by the photovoltaic cell, by electroluminescence, in response to the second injected current, and a step of detecting at least one defect in the cell on the basis of the measuring signal acquired in response to the injection of the second current;
- the photovoltaic device to be inspected belonging to a batch of a plurality of photovoltaic devices, a subset of devices is selected from the batch, qualifying tests are carried out by x-ray tomography on the selected photovoltaic devices in order to obtain a map of assembly defects, tests are carried out on the selected devices by injecting various current values, the limit current value from which the assembly defects observed by tomography also appear by electroluminescence is determined and said assembly defect detection current threshold is deduced therefrom.

The invention also relates to a system for controlling the quality of a photovoltaic device comprising a photovoltaic cell assembled with a substrate by way of an assembly interface, comprising:

- a device for injecting an electrical current through the photovoltaic cell; and
- a device for acquiring a signal measuring the light radiation emitted by the photovoltaic cell, by electroluminescence, in response to the injected current;

characterized in that the injecting device is suitable for injecting a first current having a density higher than a preset assembly defect detection current threshold, and in that it furthermore comprises a device for processing the acquired signal suitable for detecting at least one defect in the assembly interface on the basis of said acquired signal.

The invention will be better understood from the following description of one particular embodiment of the detecting method and system of the invention, given with reference to the appended drawings in which:

FIGS. 7A and 7B show images obtained from radiation emitted by electroluminescence by a cell assembled with a substrate by way of an interface, by implementing the method of FIG. 6, before and after processing, respectively.

The main function of a photovoltaic cell is to convert incident light into electricity or in other words to convert photons into electrons. Conversely, when a current is injected through the cell, by biasing the latter, the cell emits luminous radiation by electroluminescence. This effect is the result of radiative recombination of some of the injected electrons and electronic holes in the material producing photons.

Figure 1:
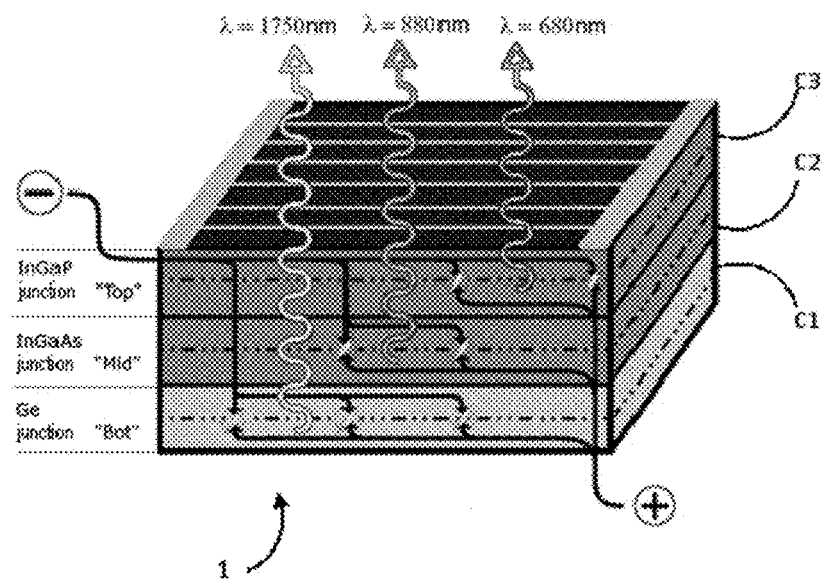
FIG. 1 shows an illustration of the electroluminescence effect applied, by way of illustrative example, to a triple junction photovoltaic cell.

The electroluminescence effect is illustrated by way of example in FIG. 1 in the particular case of a triple junction photovoltaic cell 1. This triple junction cell 1 comprises three thin superposed layers (or junctions) C1, C2 and C3, called "Bot" for the bottom layer C1, "Mid" for the middle layer C2 and "Top" for the top layer C3. In the particular example in FIG. 1, the layers C1, C2 and C3 are made from the semiconductors Ge, InGaAs and InGaP, respectively. When the cell 1 is biased, as represented by the signs "+" and "−" in FIG. 1, the three layers C1, C2 and C3 emit luminous radiation at three specific wavelengths: $\lambda_1=1750$ nm, $\lambda_2=880$ nm and $\lambda_3=680$ nm, respectively. These three wavelengths $\lambda_1$, $\lambda_2$, $\lambda_3$ characterize the cell 1.

Figure 2:
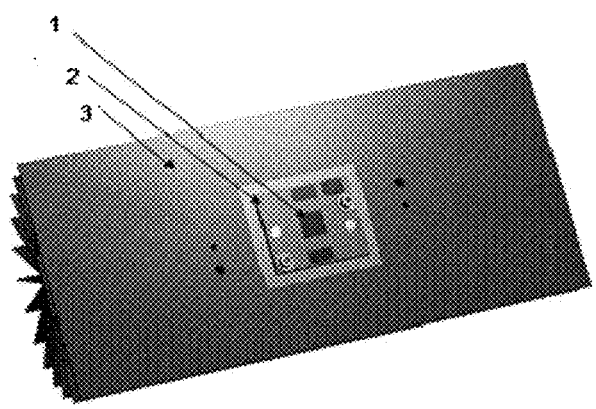
FIG. 2 shows a photovoltaic cell mounted on a thermal dissipation chain, according to one particular exemplary embodiment

Only some of the electrons injected into a photovoltaic cell produce photons by electroluminescence. The injected electrons that do not recombine radiatively produce a release of heat. To evacuate this heat, the photovoltaic cell is mounted on a thermal dissipation chain. An exemplary embodiment of such a thermal chain is shown in FIG. 2. The thermal chain shown comprises:

a substrate 2, on which the cell 1 is mounted by way of an assembly interface (not visible in FIG. 2) produced here by soldering; and a heat sink 3, on which the substrate 2 is mounted.

The term "assembly" designates the joining of initially separate entities, in the present case the substrate 2 and the cell 1.

The assembly interface is a critical element of this thermal chain. During production of this interface, here by melting of the solder, defects such as air holes, commonly referred to as voids, are liable to form. It is also possible, during the production of the assembly interface, for a foreign body to be introduced into the interface. This body is liable to significantly degrade the effectiveness of the thermal chain if its thermal conductivity is too low. During operation of the cell, these defects (voids or foreign bodies of low thermal conductivity) lead to local overheating and, therefore, decrease the effectiveness of the thermal chain.

The quality-control method and system of the invention allow such defects located in the assembly interface between a photovoltaic cell and its substrate to be detected. It may be implemented in a phase of quality-control of a photovoltaic cell assembled with its substrate, for example at the end of the manufacture of a photovoltaic panel, module or receiver containing a plurality of cells.

The method is implemented by a quality-control system made up of the following three entities:

an apparatus E1 for acquiring a signal measuring the luminous radiation emitted by the cell, by electroluminescence, in response to a current injected through the latter;

a device E2 for processing the acquired measuring signal; and a command/control device E3.

Figure 3:
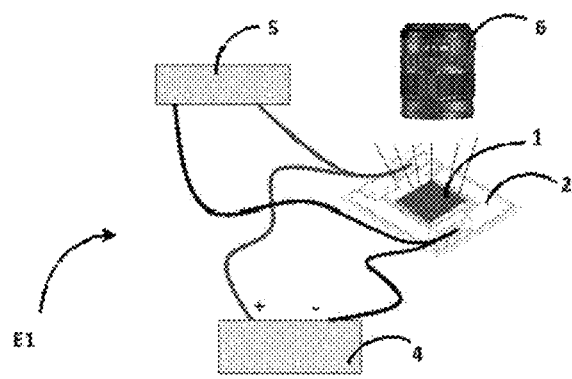
FIG. 3 shows an exemplary embodiment of an apparatus for acquiring a signal measuring the luminous radiation emitted by electroluminescence by a cell.
Figure 4:
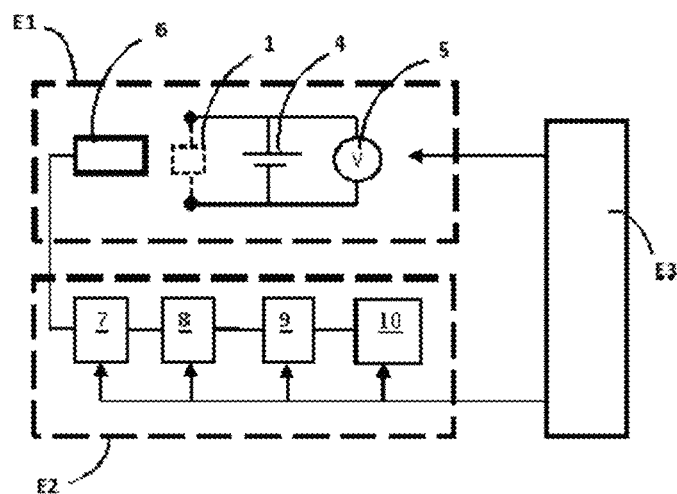
FIG. 4 shows a schematic functional block diagram of the quality-control system of the invention, according to one particular exemplary embodiment.

The acquiring apparatus E1, one exemplary embodiment of which is shown in FIG. 3, comprises a DC voltage source 4, a voltmeter 5 for controlling the applied voltage and an imaging device 6.

The voltage source 4 is intended to be connected across the terminals of the photovoltaic cell and to bias the latter, so as to inject a current through the cell. The photovoltaic cell possesses a specific current-voltage characteristic, analogous to that of a diode. The value of the voltage applied across the terminals of the cell therefore determines the value of the current injected therethrough. The voltmeter 5 is intended to control the voltage applied across the terminals of the cell. The voltmeter 5 is optional if the display of the voltage values on the supply 4 is sufficiently precise.

In operation, under the command of the command/control device E3, the source 4 applies across the terminals of the cell to be inspected:

a) a first voltage $V_1$ suitable for injecting through the cell a first current $I_1$, which is said to be "high";

b) and optionally a second voltage $V_2$ suitable for injecting through the cell a second current $I_2$, which is said to be "low".

In the first case a), the injected current value $I_1$ allows one or more defects in the assembly interface between the cell and its substrate to be detected.

In the second case b), the injected current value $I_2$ allows one or more defects in the cell itself to be detected.

By convention, a current is said to be "high" if it is higher than a given limit value and is said to be "low" if it is lower than the limit value. This limit value corresponds to a set assembly defect detection current threshold. In other words, when an injected current is higher than this threshold, it allows assembly defects to be detected using the method of the invention, as will be explained below. This limit current value, or current threshold, is here equal to 1 A·cm$^{-2}$. However, it depends on the type of cell and substrate used. It may be determined in a prior configuration step applied to a limited number of photovoltaic devices analogous to that or those to be inspected. For example, in the case of quality control of a batch of N photovoltaic devices, a subset of devices, for example x % of the N devices of the batch or a limited number p of devices of the batch, is selected therefrom. Firstly, qualifying tests are carried out by x-ray tomography on the selected photovoltaic devices in order to obtain a map of assembly defects. Next, tests are carried out on the selected devices by injecting various current values and it is determined from which limit current value the assembly defects observed by tomography also appear by electroluminescence, by applying the quality-control method of the invention, one particular embodiment of which is described below. The current threshold allowing assembly defects to be detected, corresponding to the limit current value thus determined, is deduce therefrom.

The spectral imaging device 6 is able to acquire a spectral signal measuring the luminous radiation emitted by electroluminescence, in response to an injected current, by the various points or areal elements of the emitting area of the cell. More precisely, in operation, the device 6 measures a physical quantity, here light intensity, related to the radiation emitted by emitting areal elements of the cell. The imaging device may for example be a hyperspectral camera, equipped with a matrix array of sensors able to measure a number of photons. As a variant, it may be a question of a camera able to measure the intensity of light radiation in a narrower spectral band, covering at least one of the wavelengths characterizing this cell, or even of a spectrometer. In any case, the measuring signal acquired by the device 6 makes it possible here to form a 2D image (i.e. in two dimensions) representing the emitting area of the cell in question. Each image pixel, corresponding to a point or areal element of the emitting area, is characterized by a value representative of the light intensity of the light radiation detected. In the 2D image formed, the light intensities of the various pixels may be represented, for example, by colours or colour gradients. Instead of a 2D representation of the emitting area, a 3D representation, or image, (i.e. in three dimensions) could be envisioned in which the light intensity associated with an areal element would be represented using a third dimension.

Filters may be associated with the imaging device 6, especially the hyperspectral camera, in order to select from the acquired wide-band signal one or more narrow spectral bands centred on the wavelength(s) characterizing the cell to be inspected. Each image pixel is thus characterized by a light intensity value corresponding to the light intensity of the radiation emitted at the filtered wavelength(s).

The processing device E2 is intended to process an image of the light radiation emitted by the cell taken by the camera. It comprises:

a module 7 for correcting edge effects;

a thresholding module 8;

a shape recognition module 9; and a detecting module 10.

The operation and respective roles of these various modules 7-10 will be described in more detail in the description of the method.

The command/control device E3 is connected to the various elements of the system and intended to control operation of these elements, as will be explained in the description of the detecting method.

Figure 5:
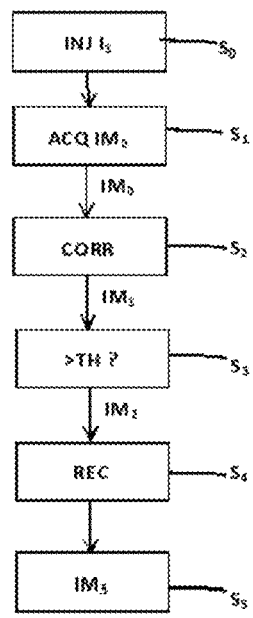
FIG. 5 shows a flowchart of the steps of the quality-control method of the invention, according to a first particular embodiment.
Figure 6:
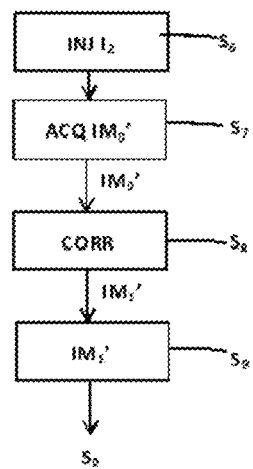
FIG. 6 shows a flow chart of the steps of the quality-control method of the invention, according to a second particular embodiment.

A first embodiment of the quality-control method of the invention will now be described with reference to FIG. 5. This first embodiment aims to detect defects in the assembly interface between a photovoltaic cell and its substrate. By way of illustrative example, the method is applied to detect (a) defect(s) in the assembly interface between the cell 1 and its substrate 2.

In a step S0 of injecting a current, the cell 1, of an area of 1 cm² in this particular and purely illustrative example, is biased by applying a voltage $V_1$ with the source 5, allowing a large injection current $I_1$ of a desired value to be obtained. For example, on account of the current-voltage characteristic of the cell 1, the voltage $V_1$ may be equal to 3.3 V and the resulting injection current $I_1$ to 15 A. With such a current value, the temperature of the cell 1 may reach a temperature of about 100° C. The voltage $V_1$ is applied in the form of a pulse, or peak, of short duration $\Delta T$. The value $\Delta T$ is comprised between 1 ms and 10 s. This duration $\Delta T$ corresponds to a time window of injection of the current $I_1$ through the cell 1. It will be noted that since the duration $\Delta T$ is very brief, the quality control does not take much time and is therefore easily usable to control the quality of the cell-substrate assembly interface at the end of manufacture.

In response to the high injected current $I_1$, the cell 1 emits luminous radiation, by electroluminescence, at the wavelengths $\lambda_1=1750$ nm, $\lambda_2=880$ nm and $\lambda_3=680$ nm that characterize the cell 1.

The step S0 of injecting of the current $I_1$ is followed by a step S1 of acquiring a measuring signal related to the luminous radiation emitted by the cell 1 in response to the injected current $I_1$. In this step S1, the imaging device 6 acquires a signal measuring the light intensity of the light radiation emitted by the cell 1. In the particular example described here, the device 6 operates in a wide spectral band covering the three wavelengths $\lambda_1=1750$ nm, $\lambda_2=880$ nm and $\lambda_3=680$ nm. It therefore detects the radiation emitted by the three layers C1, C2 and C3 of the triple junction cell 1. The signal acquired by the device 6 forms a 2D image (i.e. in two dimensions), denoted $IM_0$, representing the light-emitting area of the cell 1. Each image pixel is characterized by a light intensity value of the radiation emitted by a corresponding point or areal element of the emitting area of the cell 1 and detected by the imaging device 6.

In a step S2, the correcting module 7 carries out an operation for correcting edge effects in the image $IM_0$. Specifically, the current $I_1$ is injected into the cell 1 via busbars extending along two opposite edges of the cell 1. As a result, the density of electrons, and therefore of photons produced, is higher in the vicinity of these edges. The intensity of the light radiation emitted by the cell is therefore higher in the vicinity of the edges on which the busbars are located. Here, this is what the expression "edge effects" is understood to mean. The correcting module 7 corrects these edge effects by dividing each row of pixels of the image by the average of the projection of the image onto the axis perpendicular to the busbars. The corrected image is denoted $IM_1$. Each pixel of the image $IM_1$ is characterized by a light intensity value, possibly corrected depending on the position of the pixel.

In a step S3, the thresholding module 8 carries out an operation of thresholding the pixels of the corrected image $IM_1$. This operation consists, for each image pixel, in determining whether the intensity value characterizing this pixel is higher than or lower than a preset light intensity threshold TH. This threshold may be set manually or taught on the basis of a calibration by sampling of production units. If the light intensity value of the pixel is lower than the threshold TH, a first value, here zero, is assigned to the pixel. If the light intensity value of the pixel is higher than the threshold TH, a second value, here one, is assigned to the pixel. Thus, at the end of the thresholding step, a 2D image, denoted $IM_2$, of pixels having either the value "0" or the value "1" is obtained, the pixels at "1" corresponding to points of the cell 1 where the measured light intensity is the highest. The pixels of value 1 correspond to peaks in light intensity.

It is known that voids have ellipsoidal shapes. In the thresholded image $IM_2$ obtained at the end of the thresholding step S3, a void therefore has a substantially ellipse-shaped outline containing pixels of value 1. The thresholding step S3 is followed by a shape recognition step S4, implemented by the module 9 on the thresholded image $IM_2$. In this step S4, the module 9 identifies any ellipse shape formed by pixels of value 1 in the thresholded image $IM_2$.

In a step S5, the module 10 detects the void(s) corresponding to the ellipse-shaped zones detected in step S2 and produces a 2D map, denoted $IM_3$, of the emitting area of the cell 1 in which the void(s) detected appear.

FIGS. 7A and 7B show the image $IM_0$, i.e. before processing, and the image $IM_3$, i.e. after processing, respectively. Light intensity is represented by a greyscale. In FIG. 7B, the detected voids, referenced 11, are represented by zones that are lighter than the rest of the image.

It will be underlined here that the electroluminescent response of the cell 1 in case of injection of a high current (in the present case higher than 1 A·cm$^{-2}$) allows defects present in the assembly interface between the cell 1 and its substrate 2 to be detected. This results from the fact that a defect in the assembly interface has the effect of modifying the electroluminescent behaviour of the cell 1 itself. In the location of the cell 1 positioned plumb with the defect in the assembly interface, the intensity of the luminous radiation of wavelengths $\lambda_1$, $\lambda_2$ and $\lambda_3$ emitted by the cell 1 by electroluminescence increases. Any void-type defect in the assembly interface has an impact on the physical properties of the cell 1 and, consequently, on the electroluminescent behaviour of the latter. Thus, a void in the interface produces a heterogeneity in the emission of luminous radiation from the cell by electroluminescence. The light intensity emitted is more intense in the location of the cell under which a void is located, in the assembly interface.

The method of the invention thus consists in mapping the emission intensity of luminous radiation from the cell and detecting therein emission heterogeneities due to the presence of voids in the assembly interface between this cell and its substrate.

The cell itself may also contain defects (such as shunts—i.e. zones of preferential current flow—scratches or cracks, inter alia) liable to lead to local overheating of the cell and failure of the latter, or even destruction of the cell.

In a second embodiment of the method of the invention, on the one hand, possible structural defects in the cell are detected by injecting a low current $I_2$ and, on the other hand, possible defects in the assembly interface of the cell and of its substrate are detected by injecting a high current $I_1$.

The method according to the second embodiment comprises a first phase of detecting defects in the cell followed by a second phase of detecting voids in the assembly interface between the cell and its substrate. By way of illustrative example, the method is applied to the cell 1, to the substrate 2 and to the assembly interface.

The first detecting phase comprises a step S6 of injecting a low current $I_2$, of a value lower than 1 A·cm$^{-2}$, through the cell 1. For this purpose, the cell 1 is biased by applying a voltage $V_2$ with the source 5, allowing a low current $I_2$ of the desired value to be obtained. For example, on account of the characteristics of the cell 1, the voltage $V_2$ may be equal to 2.9 V and the injection current $I_2$ equal to 500 mA. The voltage $V_2$ is applied for a time comprised between 1 ms and 10 s.

In response to the injected current $I_2$ the cell 1 emits luminous radiation, by electroluminescence, at the wavelengths $\lambda_1=1750$ nm, $\lambda_2=880$ nm and $\lambda_3=680$ nm that characterize the cell 1.

The step S6 of injecting current is followed by a step S7 of acquiring a signal measuring the intensity of the luminous radiation emitted by the cell 1 in response to the injected current $I_2$. In this step S7, the imaging device 6 measures the light intensity of the radiation emitted by each point or areal element of the emitting area of the cell. This signal especially contains radiation emitted at the three wavelengths $\lambda_1=1750$ nm, $\lambda_2=880$ nm and $\lambda_3=680$ nm emitted by the three layers C1, C2 and C3 of the triple junction cell 1. The signal acquired by the device 6 forms a 2D image (i.e. in two dimensions), denoted $IM_0'$, representing the light-emitting area of the cell 1. Each pixel of the image $IM_0'$ is characterized by a light intensity value of the radiation emitted by a corresponding position in the emitting area of the cell 1 and detected by the imaging device 6.

The image $IM_0'$ is then corrected, in a step S8 of correcting edge effects analogous to the step S2 described above. The corrected image is denoted $IM_1'$.

The method then comprises a step S9 of detecting defects and of generating a resulting map or image denoted $IM_1'$. The step S9 consists in detecting image zones the emission of which is very different from the average emission of the image, in other words zones that are very dark or very light relative to the rest of the image. More precisely, from the light intensity values of the pixels of the image, which here has been corrected, an average emission light intensity M is calculated. Next, for each pixel, it is determined whether the light intensity average value assigned to this pixel differs from this average M by at least x %, i.e. whether the intensity value of the pixel is located outside of the range of values comprised between (M−x/100·M) and (M+x/100·M). For example, the parameter x may be about 30%. Next, zones of the image made up of pixels thus detected (the intensity value of which is outside of the above range) are identified. Structural defects do not have definite shapes, and may be a question of lines, spots or shapes of any sort. Next, the image $IM_1'$, or map, corresponding to the emitting area of the cell 1, and in which the detected defects appear, is formed.

The first phase of detecting defects in the cell 1 is followed by the second phase of detecting voids in the interface between the cell 1 and its substrate 2. In this second detecting phase the steps S0 to S5 described above are executed.

It could be envisaged to carry out the phase of detecting voids in the assembly interface before the phase of detecting defects in the cell.

The invention claimed is:

1. Method for controlling the quality of a photovoltaic device comprising a photovoltaic cell assembled with a substrate by way of an assembly interface, comprising:
   a. injecting an electrical current through the photovoltaic cell;
   b. acquiring a signal measuring the luminous radiation emitted by the photovoltaic cell, by electroluminescence, in response to the injected current;
   wherein the injection current is a first current having a density higher than a preset assembly defect detection current threshold, and
   c. detecting at least one defect in the assembly interface on the basis of said acquired measuring signal.

2. Method according to claim 1, wherein the assembly defect detection threshold is equal to 1 A·cm$^{-2}$.

3. Method according to claim 1, wherein the first current is injected in the form of a pulse of a preset duration.

4. Method according to claim 3, wherein the duration of the current pulse is comprised between 1 ms and 10 s.

5. Method according to claim 1, wherein the acquiring the luminous radiation measuring signal is synchronized with the injecting the first current.

6. Method according to claim 1, wherein from the acquired measuring signal an image representative of an emitting area of the cell is formed, each image pixel being characterized by a measured physical quantity representative of luminous radiation emitted by a corresponding areal element of the cell.

7. Method according to claim 6, comprising an operation of processing the acquired image, in which at least one image zone corresponding to a peak of said measured physical quantity is detected, the image pixels inside said zone being characterized by measured physical quantities higher than a preset threshold.

8. Method according to claim 7, wherein the processing operation comprises a thresholding producing of an image the pixels of which are associated with one or other of two preset values, depending on whether the measured physical quantity characterizing the pixel in question is lower or higher than a preset threshold.

9. Method according to claim 7, wherein the processing operation comprises recognizing shapes in the image in order to detect at least one ellipse-shaped zone.

10. Method according to claim 1, further comprising injecting a second electrical current through the photovoltaic cell, said second current having a density lower than said preset current threshold, followed by acquiring a measuring signal related to the luminous radiation emitted by the photovoltaic cell, by electroluminescence, in response to the second injected current, and detecting at least one defect in the cell on the basis of the measuring signal acquired in response to the injection of the second current.

11. Method according to claim 1, wherein the photovoltaic device to be inspected belongs to a batch of a plurality of photovoltaic devices, a subset of devices is selected from the batch, qualifying tests are carried out by x-ray tomography on the selected photovoltaic devices in order to obtain a map of assembly defects, tests are carried out on the selected devices by injecting various current values, the limit current value from which the assembly defects observed by tomography also appear by electroluminescence is determined and said assembly defect detection current threshold is deduced therefrom.

12. System for controlling the quality of a photovoltaic device comprising a photovoltaic cell assembled with a substrate by way of an assembly interface, comprising:
   a. a device for injecting an electrical current through the photovoltaic cell;
   b. a device for acquiring a signal measuring the luminous radiation emitted by the photovoltaic cell, by electroluminescence, in response to the injected current;
   wherein the injecting device is suitable for injecting a first current having a density higher than a preset assembly defect detection current threshold, and c. a device for processing the acquired signal suitable for detecting at least one defect in the assembly interface on the basis of said acquired signal.

13. System according to claim 12, wherein the injecting device is suitable for injecting a first current having a density higher than 1 A·cm$^{-2}$.

14. System according to claim 12, wherein the injecting device is suitable for injecting a current pulse of duration comprised between 1 ms and 10 s.

15. System according to claim 12, wherein the injecting device and the acquiring device are suitable for synchronising the current injection and the acquisition of the measuring signal.

16. Method according to claim 2, wherein the first current is injected in the form of a pulse of a preset duration.

17. Method according to claim 16, wherein the duration of the current pulse is comprised between 1 ms and 10 s.

18. Method according to claim 8, wherein the processing operation comprises recognizing shapes in the image in order to detect at least one ellipse-shaped zone.

19. System according to claim 13, wherein the injecting device is suitable for injecting a current pulse of duration comprised between 1 ms and 10 s.

20. System according to claim 13, wherein the injecting device and the acquiring device are suitable for synchronising the current injection and the acquisition of the measuring signal.

21. System for controlling the quality of a photovoltaic device comprising a photovoltaic cell assembled with a substrate by way of an assembly interface, comprising:

a. a voltage source configured to inject an electrical current through the photovoltaic cell;

b. an imaging device configured to acquire a signal measuring the luminous radiation emitted by the photovoltaic cell, by electroluminescence, in response to the injected current;

wherein the voltage source is configured to inject a first current having a density higher than a preset assembly defect detection current threshold, and c. a processor configured to process the acquired signal suitable for detecting at least one defect in the assembly interface on the basis of said acquired signal.

\* \* \* \* \*